(12) United States Patent
Zhou

(10) Patent No.: US 12,285,316 B1
(45) Date of Patent: Apr. 29, 2025

(54) AIRBAG-TYPE EARPLUG COMFORTABLE TO WEAR AND OFFERING SOUND INSULATION AND NOISE REDUCTION

(71) Applicant: Xiangrong Zhou, Shenzhen (CN)

(72) Inventor: Xiangrong Zhou, Shenzhen (CN)

( * ) Notice: Subject to any disclaimer, the term of this patent is extended or adjusted under 35 U.S.C. 154(b) by 0 days.

(21) Appl. No.: 18/814,592

(22) Filed: Aug. 26, 2024

(30) Foreign Application Priority Data

Jul. 23, 2024 (CN) .......................... 202421755214.5

(51) Int. Cl.
*A61F 11/08* (2006.01)
*A61F 11/10* (2006.01)

(52) U.S. Cl.
CPC .................................... *A61F 11/10* (2013.01)

(58) Field of Classification Search
CPC ........ A61F 11/06; A61F 11/08; A61F 11/085; A61F 11/10
See application file for complete search history.

(56) References Cited

U.S. PATENT DOCUMENTS

| 2,541,520 | A | * | 2/1951 | Kegel | ..................... | A61H 21/00 |
| | | | | | | 73/714 |
| 2,876,767 | A | * | 3/1959 | Wasserman | ............. | A61F 11/10 |
| | | | | | | 128/865 |
| 3,110,356 | A | * | 11/1963 | Mendelson | ............. | A61F 11/10 |
| | | | | | | 128/865 |
| 4,834,211 | A | * | 5/1989 | Bibby | .................. | H04R 25/656 |
| | | | | | | 381/328 |

* cited by examiner

*Primary Examiner* — Camtu T Nguyen
(74) *Attorney, Agent, or Firm* — Novoclaims Patent Services LLC; Mei Lin Wong

(57) ABSTRACT

The utility model discloses an airbag-type earplug comfortable to wear and offering sound insulation and noise reduction, which comprises a support part and an airbag part, a through ventilation channel is arranged in the middle of the support part, the airbag part is arranged outside the support part, and the whole airbag part is in the shape of a frustum, that is, an internal cavity of the airbag part gradually expands outward from one end to the other. This utility model can adaptively adjust to the size of different individuals' ear canals, providing a better fit and addressing the issues of sound leakage and ear swelling associated with traditional silicone and foam earplugs. Furthermore, a metal filter allows for the adjustment of micropore sizes from 1 μm to 40 μm according to different scenarios, overcoming the limitation of common foam filters on the market that cannot be washed.

6 Claims, 3 Drawing Sheets

AIRBAG-TYPE EARPLUG COMFORTABLE TO WEAR AND OFFERING SOUND INSULATION AND NOISE REDUCTION

CROSS REFERENCE OF RELATED APPLICATION

This is a non-provisional application that claims priority to Chinese application number 2024217552145, filing date Jul. 23, 2024, the entire contents of each of which are expressly incorporated herein by reference.

BACKGROUND OF THE PRESENT INVENTION

The utility model belongs to the technical field of noise reduction, and particularly relates to an airbag-type earplug comfortable to wear and offering sound insulation and noise reduction.

DESCRIPTION OF RELATED ARTS

Anti-noise earplugs (sound insulation earplugs, noise reduction earplugs, sleep earplugs) are usually made from silicone or low-pressure foam sponge material, and high-elasticity polyester material. After being inserted into the ear canal, the earplugs press tightly against the ear canal to prevent sound from entering the middle ear and inner ear (eardrum), achieving the purpose of sound isolation and allowing for a quiet resting or working environment.

The existing noise-cancelling earplugs made from foam sponge cannot be used repeatedly, as they are prone to bacterial growth. The existing silicone noise-cancelling earplugs are reusable through washing, but they have a high structural support strength, which can cause ear discomfort and pain from over-compression, and prolonged use may result in headaches and dizziness. Additionally, the existing silicone noise-cancelling earplugs cannot automatically adjust their size, thus failing to meet the needs of a majority of consumers with a one-size-fits-all solution. Consequently, manufacturers often provide several different sizes (large, medium, and small) of ear tips for consumer selection, and the ear tips that do not fit are often discarded, leading to both inconvenience and resource wastage.

SUMMARY OF THE PRESENT INVENTION

This utility model provides an airbag-type earplug comfortable to wear and offering sound insulation and noise reduction to solve the above technical problems.

To achieve the technical effect, the utility model adopts the following solution.

An airbag-type earplug comfortable to wear and offering sound insulation and noise reduction comprises a support part and an airbag part, the airbag part is arranged outside the support part, and the whole airbag part is in the shape of a frustum, that is, an internal cavity of the airbag part gradually expands outward from one end to the other.

Preferably, a thickness of a cavity wall located outside a small cavity on the airbag part is smaller than that of a cavity wall located outside a large cavity on the airbag part.

Preferably, a through ventilation channel is arranged in the support part.

Preferably, the airbag-type earplug comfortable to wear and offering sound insulation and noise reduction further comprises a metal filter which is arranged in the ventilation channel.

Preferably, one end of the support part is provided with a hand lever, and a tail end of the hand lever is provided with a cord threading hole.

Preferably, a clearance groove is reserved between the outside of the support part and an expansion portion of the airbag part.

Preferably, two ends of the airbag part are provided with sealing rings respectively, sealing grooves are formed in outer sides of two ends of the support part respectively, and the two sealing rings are interference-fitted into the two sealing grooves respectively.

Preferably, one end of the airbag part is provided with a first sealing ring, the other end of the airbag part is integrally connected with one end of a supporting sleeve pillar, and an outer side of the other end of the supporting sleeve pillar is provided with a first sealing groove; the first sealing ring is able to be flipped and then interference-fitted into the first sealing groove; second sealing rings are arranged on inner sides of two ends of the supporting sleeve pillar respectively; and sealing grooves are formed in outer sides of two ends of the support part respectively, and the two second sealing rings are able to be interference-fitted into the two sealing grooves respectively.

Preferably, a second sealing groove is formed in an outer side of the support part, one end of the airbag part is provided with a second sealing ring, and the second sealing ring is interference-fitted into the second sealing groove, so that the support part is sleeved with the airbag part; and the other end of the airbag part is closed, and the closed end of the airbag part is arranged at one end of the support part in a blocking manner to seal one end of the ventilation channel.

The utility model has the beneficial effects that: based on the soft and easily deformable characteristics of an airbag and the fact that an entry end of the airbag is small and can easily enter the ear, the ear canal first contacts and presses an expansion end of the airbag, and then presses the entry end to be gradually level with the expansion end, so that the airbag and the ear canal can fit closely, realizing good airtightness; further, the force on an airbag fitting surface is uniform, eliminating wrinkles and gaps that cause sound leakage and solving the problem of sound leakage of traditional earplugs; and the utility model also addresses the issue of ear swelling associated with conventional earplugs on the market.

Figure 1:
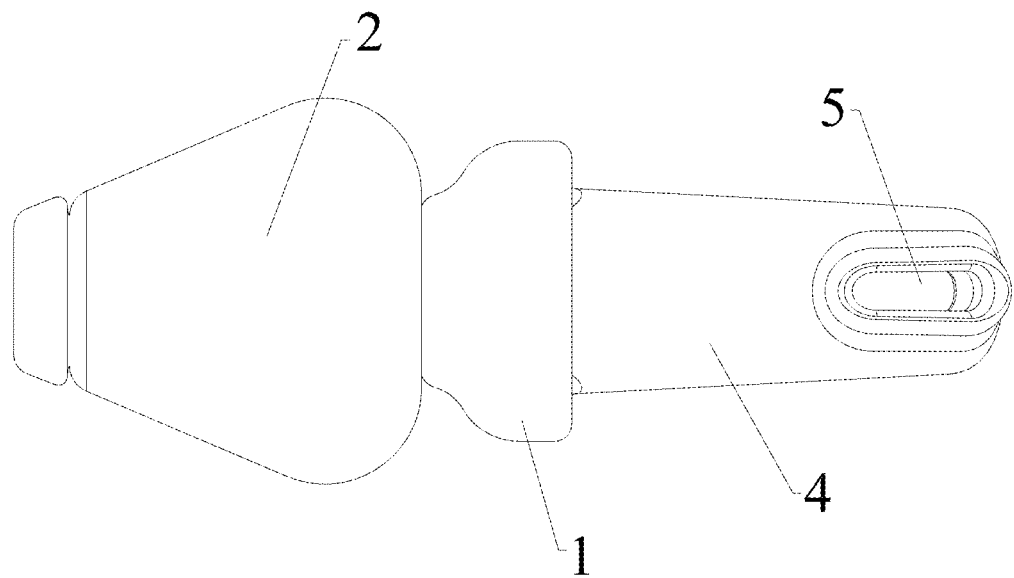
FIG. 1 is a top view of a noise reduction earplug according to an embodiment of the utility model.

Description of reference numerals: 1—support part, 2—airbag part, 3—metal filter, 4—hand lever, 5—cord threading hole, 6—clearance groove, 7—sealing ring, 8—sealing groove, 9—first sealing ring, 10—supporting sleeve pillar, 11—first sealing groove, 12—second sealing ring, 13—second sealing groove, 14—second sealing ring.

DETAILED DESCRIPTION OF THE PREFERRED EMBODIMENT

In order to make the object, technical solutions and advantages of the utility model clearer, the following detailed description of the utility model is given in conjunction with attached drawings and embodiments. It should be understood that the specific embodiments described here are only for explaining the utility model, and do not limit the utility model. It should be noted that when an element is described as being "fixed to" or "arranged on" another element, it may be directly on another element or there may be intervening elements. When an element is described as being "connected to" another element, it may be directly connected to another element or there may be intervening elements. When an element is described as being "fixedly connected to" another element, common fixing methods such as welding, bolting, or adhesive bonding may be adopted.

Figure 2:
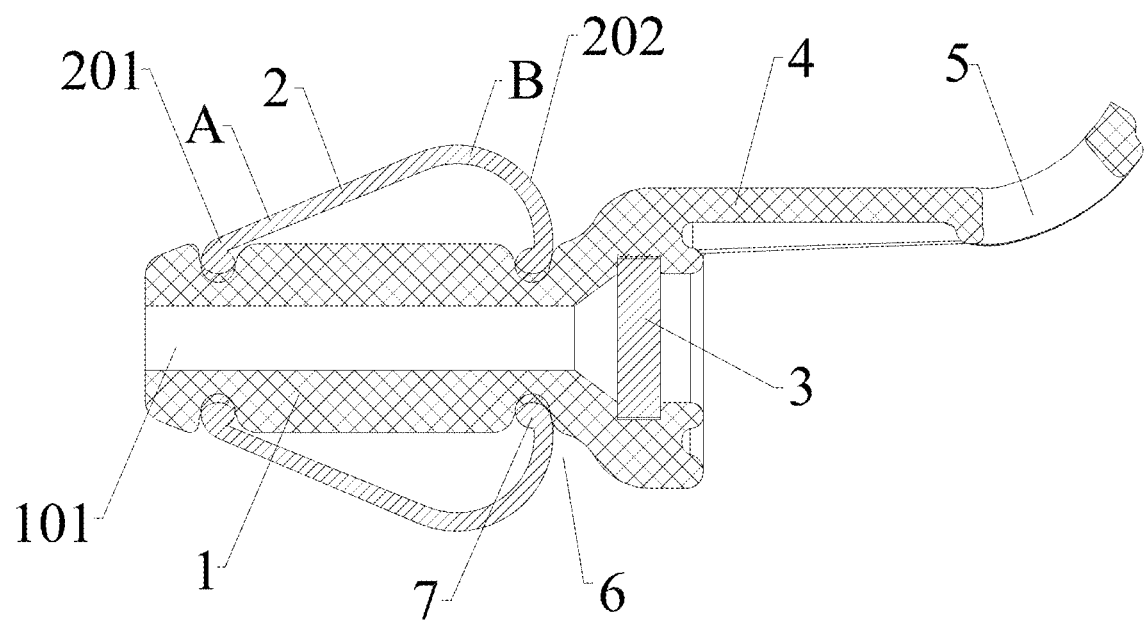
FIG. 2 is a side sectional view of a noise reduction earplug according to an embodiment of the utility model.
Figure 3:
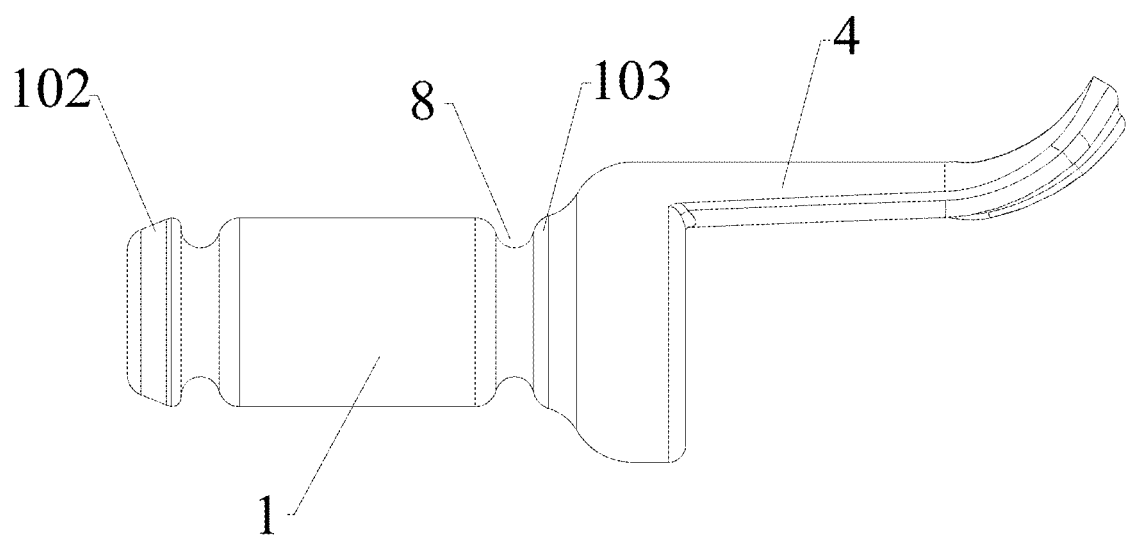
FIG. 3 is a schematic diagram of a support part according to an embodiment of the utility model.

Referring to FIG. 1-FIG. 3, a preferred embodiment of the utility model discloses an airbag-type earplug comfortable to wear and offering sound insulation and noise reduction, which comprises a support part 1 having a first end 102 and a second end 103 and an airbag part 2, the airbag part 2 is arranged outside the support part 1, and the whole airbag part 2 having a front end 201 and a rear end 202, is in the shape of a frustum, that is, an internal cavity of the airbag part 2 gradually expands outward from one end to the other.

Specifically, a thickness of a cavity wall A located outside a small cavity on the airbag part 2 is smaller than that of a cavity wall B located outside a large cavity on the airbag part 2. When the part B is pressed tightly by the ear canal, air pressure flows towards part A, making it easier to expand part A, changing the original frustum shape to a straight cylindrical shape, and increasing the contact area between the airbag part 2 and the ear canal.

Specifically, a through ventilation channel 101 is arranged in the support part, ensuring good ventilation outside the ear canal.

Specifically, the airbag-type earplug comfortable to wear and offering sound insulation and noise reduction further comprises a metal filter 3 which is arranged in the ventilation channel. The metal filter 3 is a microporous sponge structure, which can effectively reduce noise, and ensure good ventilation outside the ear canal, thus reducing the discomfort such as tinnitus and dizziness caused by long-term wearing of the earplug. Compared with conventional sponge filters, the metal filter 3 allows for more convenient adjustment of micropore sizes, and the micropore aperture can be customized from 1 μm to 40 μm. It effectively reduces noise within the frequency range of 20 Hz to 8000 Hz and also overcomes the limitation of foam filters that cannot be washed.

Specifically, one end of the support part 1 is provided with a hand lever 4, making it convenient to hold and push the entire earplug by hand; and a tail end of the hand lever 4 is provided with a cord threading hole 5, allowing for the threading of a cord.

Specifically, a clearance groove 6 is reserved between the outside of the support part 1 and an expansion portion of the airbag part 2. When the ear canal is small, pressure on part B can be directed towards the clearance groove 6, causing the cylindrical body formed after the deformation of the airbag part 2 to become slender, thus reducing the excessive pressure of the airbag part 2 on the ear canal and minimizing discomfort during use.

Specifically, two ends of the airbag part 2 are provided with sealing rings 7 respectively, sealing grooves 8 are formed in outer sides of two ends of the support part respectively, and the two sealing rings 7 are interference-fitted into the two sealing grooves 8 respectively.

Figure 4:
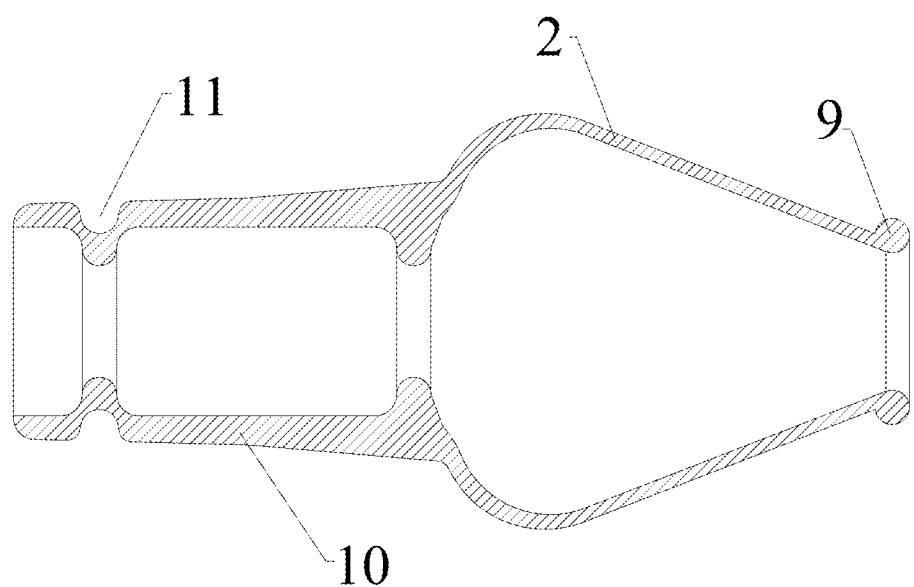
FIG. 4 is a schematic diagram of an airbag part in an unflipped state according to a second embodiment of the utility model.
Figure 5:
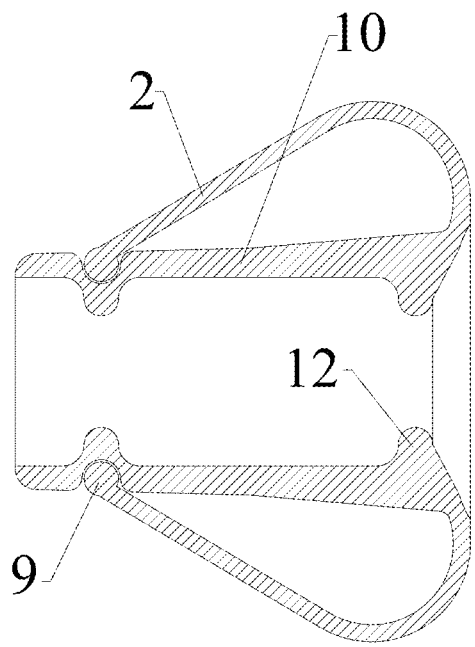
FIG. 5 is a schematic diagram of an airbag part in a flipped state according to a second embodiment of the utility model.
Figure 6:
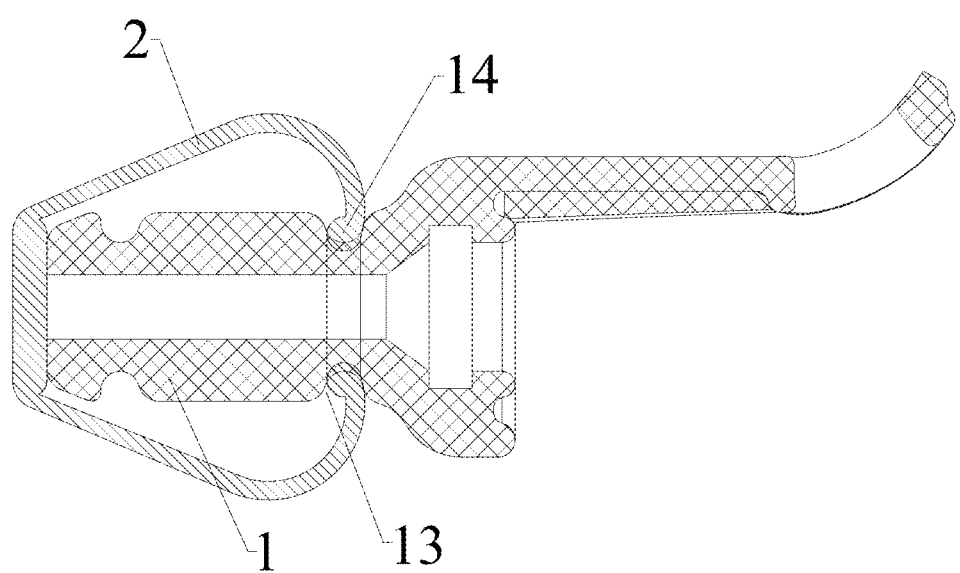
FIG. 6 is a side sectional view of a noise reduction earplug according to a third embodiment of the utility model.

Referring to FIG. 4-FIG. 6, a second preferred embodiment of the utility model discloses an airbag-type earplug comfortable to wear and offering sound insulation and noise reduction, with all structures, except for the airbag part 2, being the same as in the first preferred embodiment. One end of the airbag part 2 is provided with a first sealing ring 9, the other end of the airbag part 2 is integrally connected with one end of a supporting sleeve pillar 10, and an outer side of the other end of the supporting sleeve pillar 10 is provided with a first sealing groove 11; the first sealing ring 9 is able to be flipped and then interference-fitted into the first sealing groove 11; second sealing rings 12 are arranged on inner sides of two ends of the supporting sleeve pillar 10 respectively; and sealing grooves 8 are formed in outer sides of two ends of the support part 1 respectively, and the two second sealing rings 12 are able to be interference-fitted into the two sealing grooves 8 respectively. In this scheme, the supporting sleeve pillar 10 is added to the airbag part. By arranging the supporting sleeve pillar 10 outside the support part 1 in a sleeving mode, as opposed to directly arranging the soft airbag part 2 outside the support part 1 in a sleeving mode in the previous scheme, the installation process is more convenient and stable, and the process of flipping and interference-fitting the first sealing ring 9 in the first sealing groove 10 is also simpler.

Referring to FIG. 6, a third preferred embodiment of the utility model discloses an airbag-type earplug comfortable to wear and offering sound insulation and noise reduction, with all structures, except for the airbag part, being the same as in the first preferred embodiment. A second sealing groove 13 is formed in an outer side of the support part 1, one end of the airbag part 2 is provided with a second sealing ring 14, and the second sealing ring 14 is interference-fitted into the second sealing groove 13, so that the support part 1 is sleeved with the airbag part 2; and the other end of the airbag part 2 is closed, and the closed end of the airbag part 2 is arranged at one end of the support part 1 in a blocking manner to seal one end of the ventilation channel. This embodiment is suitable for environments where blocking external impurities is a priority.

From the above description, it can be seen that this utility model can effectively adjust to ear canals of different sizes, solving the problems of traditional earplugs being prone to sound leakage and regular earplugs in the market leading to ear swelling.

The preferred embodiments of the utility model have been described in detail in combination with the attached drawings. It should be noted that the protection scope of the utility model includes but is not limited to the above embodiments. The specific structures disclosed in the attached drawings in the specification are only preferred embodiments of the utility model, and other embodiments can be developed by those skilled in the art on this basis. Any simple deformation or equivalent replacement that does not deviate from the innovative concept of the utility model is covered by the utility model and belongs to the protection scope of the utility model.

What is claimed is:

1. An airbag-type earplug comfortable to wear and offering sound insulation and noise reduction, comprising:
   a support part defining a first end and a second end opposite the first end; and
   an airbag part having a front end and a rear end, the airbag part being positioned external to the support part, and the airbag part having a shape of a frustum defining a cavity gradually expanding from the front end to the rear end;
   wherein each of the first end and the second end of the support part has a sealing groove formed therein;
   wherein each of the front end and the rear end of the airbag part is provided with a sealing ring;
   wherein the sealing rings are interference-fitted into the sealing grooves, respectively.

2. The airbag-type earplug comfortable to wear and offering sound insulation and noise reduction according to claim 1, wherein a wall B of the cavity located at the rear end of the airbag part is thicker than a wall A of the cavity located at the front end of the airbag part.

3. The airbag-type earplug comfortable to wear and offering sound insulation and noise reduction according to claim 1, wherein a channel is arranged within the support part extending between the first end and the second end of the support part.

4. The airbag-type earplug comfortable to wear and offering sound insulation and noise reduction according to claim 3, further comprising a metal filter positioned in the channel.

5. The airbag-type earplug comfortable to wear and offering sound insulation and noise reduction according to claim 1, wherein further comprising a hand lever extended rearwardly from the second end of the support, wherein the hand lever is provided with a cord-threading hole.

6. The airbag-type earplug comfortable to wear and offering sound insulation and noise reduction according to claim 1, further comprising a clearance groove being provided between the second end of the support part and the rear end of the airbag part, the clearing groove adapted to reduce excessive pressure of the airbag part on the ear canal during use.

* * * * *